(12) United States Patent
Maschke

(10) Patent No.: US 7,974,678 B2
(45) Date of Patent: Jul. 5, 2011

(54) CATHETER FOR MAGNETIC NAVIGATION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1884 days.

(21) Appl. No.: 10/804,707

(22) Filed: Mar. 19, 2004

(65) Prior Publication Data

US 2004/0242995 A1     Dec. 2, 2004

(30) Foreign Application Priority Data

Mar. 21, 2003 (DE) .................. 103 13 868

(51) Int. Cl.
*A61B 5/05* (2006.01)
(52) U.S. Cl. ........ 600/409; 600/422; 600/423; 600/431; 600/433; 606/130
(58) Field of Classification Search .................. 600/407, 600/409, 422, 431, 433, 423, 424, 417, 100, 600/101; 128/653.5, 899; 606/130; 324/260; 361/141
See application file for complete search history.

(56) References Cited

U.S. PATENT DOCUMENTS

| | | | | |
|---|---|---|---|---|
| 4,249,536 A * | 2/1981 | Vega | ................ | 604/98.01 |
| 4,771,772 A * | 9/1988 | DeWitt | ................ | 604/892.1 |
| 5,089,006 A * | 2/1992 | Stiles | ................ | 623/1.1 |
| 5,845,646 A * | 12/1998 | Lemelson | ................ | 128/899 |
| 5,931,818 A | 8/1999 | Werp et al. | ................ | 604/270 |
| 6,052,610 A | 4/2000 | Koch | ................ | 600/424 |
| 6,058,323 A * | 5/2000 | Lemelson | ................ | 600/408 |
| 6,148,823 A | 11/2000 | Hastings | | |
| 6,216,026 B1 | 4/2001 | Kuhn et al. | ................ | 600/409 |
| 6,233,474 B1 * | 5/2001 | Lemelson | ................ | 600/411 |
| 6,241,671 B1 | 6/2001 | Ritter et al. | | |
| 6,258,098 B1 * | 7/2001 | Taylor et al. | ................ | 606/108 |
| 6,286,514 B1 * | 9/2001 | Lemelson | ................ | 128/899 |
| 6,292,678 B1 | 9/2001 | Hall et al. | | |
| 6,293,282 B1 * | 9/2001 | Lemelson | ................ | 128/899 |
| 6,321,106 B1 * | 11/2001 | Lemelson | ................ | 600/407 |
| 6,327,492 B1 * | 12/2001 | Lemelson | ................ | 600/434 |
| 6,330,467 B1 | 12/2001 | Creighton, IV et al. | | |
| 6,400,980 B1 * | 6/2002 | Lemelson | ................ | 600/478 |
| 6,401,723 B1 | 6/2002 | Garibaldi et al. | ................ | 128/899 |
| 2002/0103430 A1 * | 8/2002 | Hastings et al. | ................ | 600/411 |

FOREIGN PATENT DOCUMENTS

WO     WO 02/07794     1/2002

* cited by examiner

*Primary Examiner* — Tse Chen
*Assistant Examiner* — Elmer Chao
(74) *Attorney, Agent, or Firm* — Schiff Hardin LLP

(57) ABSTRACT

A catheter for magnetic navigation in the human body, has a magnet arranged in the catheter tip in order to move a catheter to the desired position in the body by interaction with an external magnetic field, and has a number of separated electromagnets, that can be controlled independently of one another, distributed along the length of the catheter body.

3 Claims, 2 Drawing Sheets

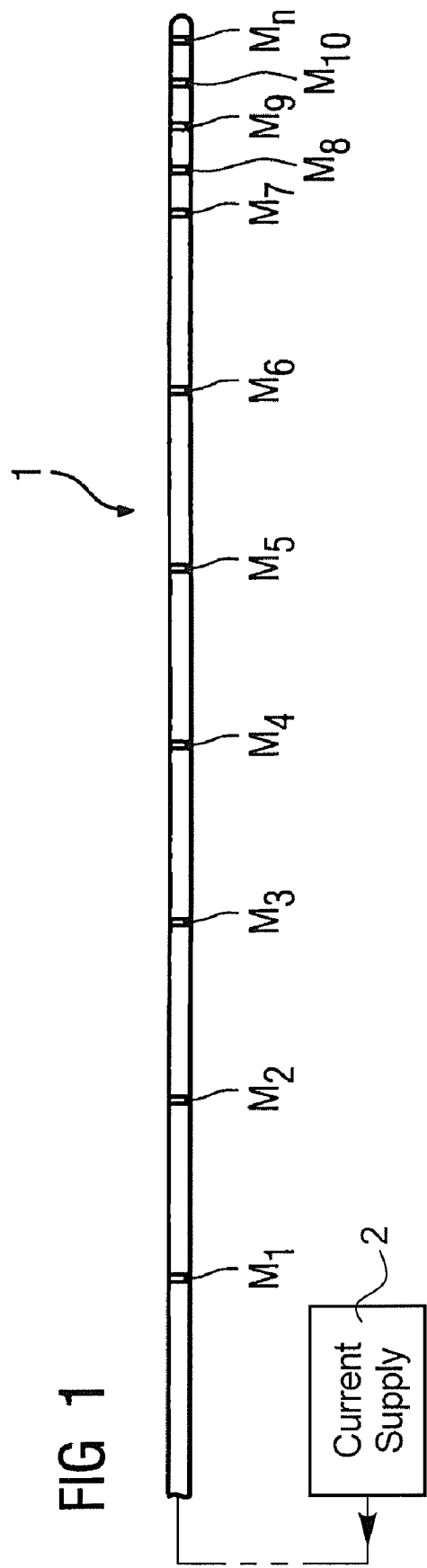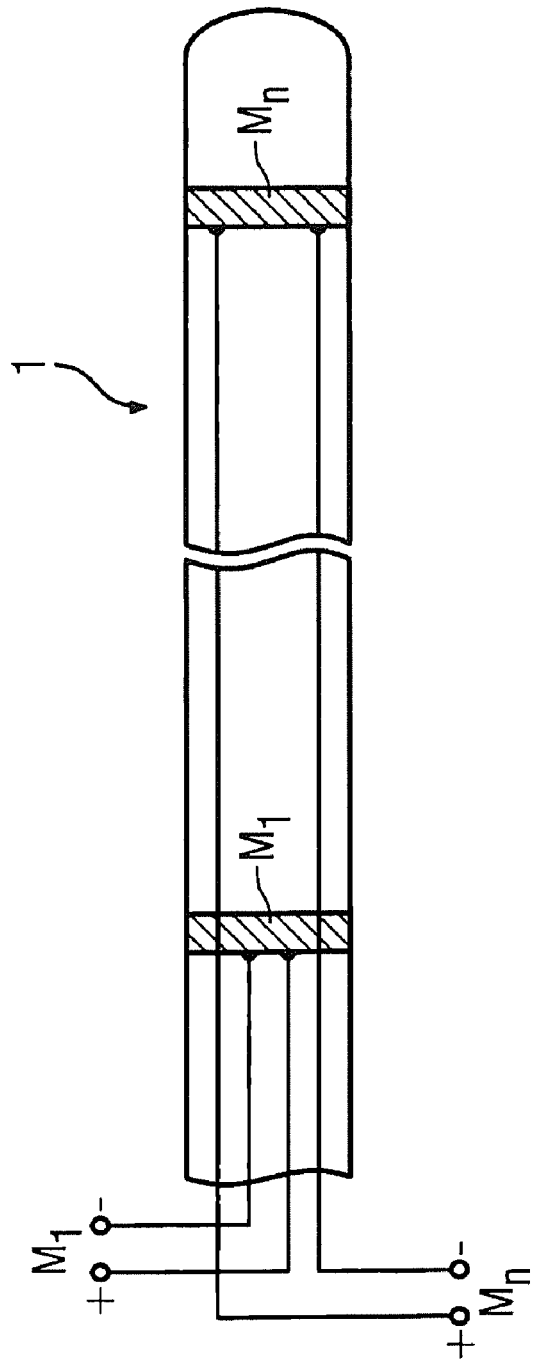
FIG 1
FIG 2

CATHETER FOR MAGNETIC NAVIGATION

BACKGROUND OF THE INVENTION

1. Field of the Invention

The present invention concerns a catheter for magnetic navigation in the human body, of the type having a magnet arranged in the catheter tip, in order to move the catheter to a desired location in the body using an external magnetic field.

2. Description of the Prior Art

Catheters of the above type, that are presently being tested in a number of clinics, already have become known in different embodiments. In addition to catheters in which the magnet in the catheter tip is a permanent magnet (U.S. Pat. Nos. 6,148,823, 6,330,467 and 6,241,671), additional catheters have been proposed in which a electromagnet is arranged in the catheter tip (U.S. Pat. No. 6,401,723). This guidance of the catheter in the human body with using a magnet arranged in the tip, that effectively "pulls" the following catheter body through the body, is hindered in the case of movement in vessels with very narrow curves and divergences by the rigidity of the known catheter body. This leads to a significant counter-force that tries to pull the catheter back from the already-achieved position.

SUMMARY OF THE INVENTION

An object of the present invention is to provide a catheter of the type described above that allows even catheters having a relatively rigid catheter body to be pushed into a multiply-branched and twisting vessel tree without problems.

This object is achieved in accordance with the invention by a catheter having a number of separated electromagnets, which can be controlled independently of one another, distributed along the length of the catheter body.

Different sections of the catheter can be provided simultaneously with different magnetic moments by the inventive electromagnets distributed along the catheter body length, which has the effect that, for example, individual sections of the catheter body in the vessels can be given with a magnetic moment that holds the catheter body in a position, and other sections are given with a magnetic moment that applies a force for a forward/backward motion, similar to the manner of movement of a snake.

In an embodiment of the invention the magnet in the tip can be composed of either a permanent magnet or a further electromagnet.

If the multiple magnets are activated with a synchronously-clocked current, a forward/backward motion of the catheter similar to a magnetic linear drive can be achieved.

DESCRIPTION OF THE DRAWINGS

FIG. 1 is a side view of an inventive catheter,

FIG. 2 is an enlarged, partially fragmented section through an inventive catheter.

DESCRIPTION OF THE DRAWINGS

Figure 3:
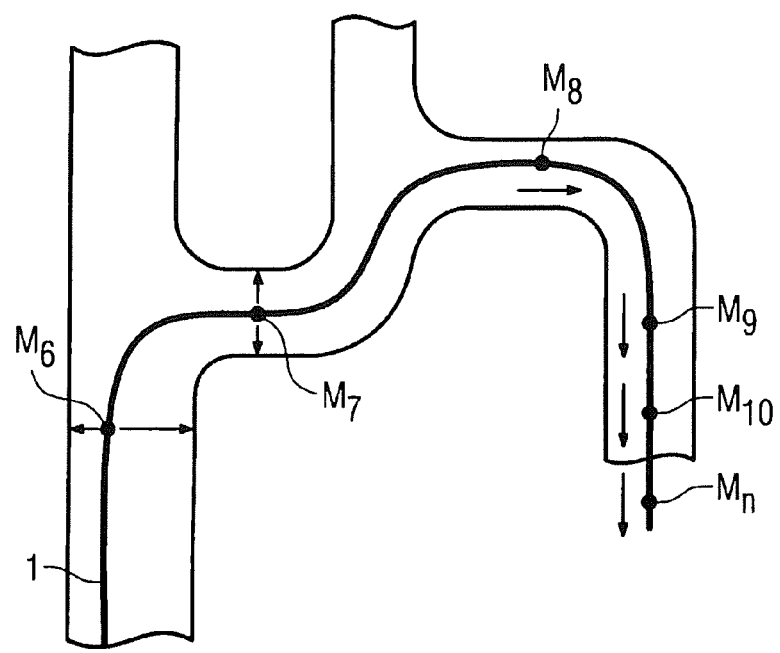
FIG. 3 is a schematic illustration of a vessel tree with an inventive catheter therein the electromagnets of which are given different magnetic moments.

The catheter body 1 shown in FIG. 1 has a number of separated magnets $M_1$-$M_n$ distributed along its length, with the magnet $M_n$ adjacent to the catheter tip being formed by either an electromagnet or a permanent magnet. Each remaining magnet $M_1$-$M_{n-1}$ is an electromagnet that, as can in particular be seen from FIG. 2, can be controlled independently of one another with current from an external current supply 2 shown in FIG. 1, such that they can be provided with respective magnetic moments that differ from each other.

FIG. 3 schematically shows a vessel tree with divergences which should be navigated with the aid if an inventive catheter, whereby an external magnetic field exists to exert a corresponding pulling force on the magnets of the catheter not being shown in FIG. 3. The interaction, especially of the navigation magnets arranged in the catheter tip with a magnetic field in order to pull the catheter through the vessel tree, is known and repeatedly specified in the prior art, and thus needs no detailed explanation at this point.

In order to counteract the reaction of the rigid catheter body 1, that tends to flex or curve back into its original position upon being deformed, and thus to prevent these reactions from pulling the catheter body 1 back from its already-achieved position, the electromagnets $M_1$-$M_n$ are controlled with current in different manners, such that they develop different effects in the external magnetic field, and in particular become fixed at particular locations of the catheter body 1, such that the aforementioned retraction motions can not occur at all.

In the exemplary embodiment, the magnet M6 and the magnet M7 are provided with suitable current control to provide a magnetic moment so that the catheter body 1 is held in the magnetic field, while the magnets M8-$M_n$ produce a magnetic moment that effects a motion in the forward direction.

The invention is not limited to the shown exemplary embodiment. The distribution of the magnets can ensue in a different manner, as long as instead of only one magnet (typically arranged non-distal), a number of distributed electromagnets are provided that can experience different holding and pulling forces in the external navigation magnetic field by being differently charged with current.

Although modifications and changes may be suggested by those skilled in the art, it is the intention of the inventor to embody within the patent warranted hereon all changes and modifications as reasonably and properly come within the scope of his contribution to the art.

I claim as my invention:

1. A catheter for magnetic navigation in a human body by interacting with an external magnetic field, said catheter comprising:
    an elongated catheter body terminating in a catheter tip;
    a magnet disposed at said catheter tip adapted to interact with said external magnetic field to move said catheter to a desired position in a human body;
    a plurality of separated, independently controllable electromagnets disposed along said catheter body; and
    a current supply connected to said plurality of electromagnets to supply respective synchronously-clocked currents thereto to cause said plurality of electromagnets with current supplied thereto to exhibit respectively different magnetic moments.

2. A catheter as claimed in claim 1 wherein said magnet at said catheter tip is a permanent magnet.

3. A catheter as claimed in claim 1 wherein said magnet at said catheter tip is an electromagnet.

* * * * *